United States Patent [19]

Mathur

[11] 4,096,240

[45] Jun. 20, 1978

[54] SKIN LIGHTENING COMPOSITION AND METHOD

[75] Inventor: Girish Prasad Mathur, Bombay, India

[73] Assignee: Lever Brothers Company, New York, N.Y.

[21] Appl. No.: 675,570

[22] Filed: Apr. 9, 1976

[30] Foreign Application Priority Data

Apr. 10, 1975 United Kingdom ............... 14825/75

[51] Int. Cl.$^2$ .............................................. A61K 7/42
[52] U.S. Cl. ....................................... 424/59; 424/47; 424/60; 424/62
[58] Field of Search ................................... 424/59, 62

[56] References Cited

U.S. PATENT DOCUMENTS

| 3,892,844 | 7/1975 | Erlemann ................................ 424/59 |
| 3,937,810 | 2/1976 | Mathur et al. ......................... 424/59 |

FOREIGN PATENT DOCUMENTS

| 2,096,712 | 2/1972 | France ................................ 424/59 |
| 212,943 | 5/1967 | Sweden ............................... 424/59 |

OTHER PUBLICATIONS

Chem. Abs., 1955, vol. 49, p. 14273.

*Primary Examiner*—Dale R. Ore
*Attorney, Agent, or Firm*—Michael J. Kelly; Melvin H. Kurtz; James J. Farrell

[57] ABSTRACT

A cosmetic composition for topical application to human skin contains niacinamide, or a precursor thereof, for lightening the skin, together with an ultraviolet absorbing sunscreen to protect against subsequent sunburn or suntan. Preferably more than one sunscreen is employed to provide for protection over a wide UV spectrum. The active ingredients of the composition can be provided for use as a cream, lotion, aerosol spray or in other classical forms by employing an appropriate vehicle.

18 Claims, No Drawings

SKIN LIGHTENING COMPOSITION AND METHOD

The invention relates to skin cosmetic compositions which have a lightening effect on the skin.

In British Pat. No. 1,370,236 there is described a composition intended for application to the skin which contains niacin as a skin lightening agent. The method by which niacin acts to effect skin lightening is postulated as being a retardation of melanin dispersion or distribution into the epidermis.

We have now discovered that niacinamide and compounds releasing niacinamide on the skin can also act as skin lightening agents, it being apparent that niacinamide probably acts by a mechanism similar to that of niacin, although it does not appear to exhibit any unpleasant skin flushing reaction due to vasodilation of the peripheral blood vessels such as has been observed with niacin.

Furthermore, we have found that niacinamide is easier to formulate into compositions for application to the skin than is niacin, and also that niacinamide is more readily absorbed by the skin than is niacin.

It is accordingly one object of the invention to provide an improved cosmetic composition which is capable of lightening the skin.

In contrast, certain skin compositions have also been formulated for the purpose of maintaining the colour of skin against darkening following exposure to ultra-violet light; these compositions have generally been based on materials which deflect and scatter incident ultra-violet light of the wavelength which produces burning and tanning of the skin, or which absorbs this light.

It will be appreciated that sunburn, melanogenesis, and pigmentation of the skin are closely associated responses to irradiation by the erthemogenic spectrum. The photobiological changes that cause erythema also lead to melanogenesis and increased pigmentation. The so-called erythemogenic spectrum is generally considered to include wavelengths between 290 and 320 nm, with peaks at 297 or 300 - 207 nm. Light of wavelengths greater than 320 nm is thought to produce erythema.

The increase of melanin pigment that follows exposure of skin to solar radiation or ulatra-violet light from artificial sources involves two distinct photobiological processes:

(i) immediate pigment darkening of performed pigment without induction of erythema, and
(ii) the primary melanization involving induction of erythema, formation of new pigment and its dispersion.

The wavelengths which lie in the range of 320–420 nm with a broad maximum at 420 nm are responsible for the immediate pigment darkening in skin of preformed pigment without induction of erythema. Primary melanisation is most effectively initiated by wavelengths shorter than 320 nm.

It is accordingly a further object of the invention to provide an improved composition for topical application to the skin which not only lightens the skin but which also imparts protection from the immediate pigment darkening and the primary melanization due to exposure to solar radiation, thus prolonging the lightening effect.

According to the invention, there is provided a cosmetic composition for lightening human skin following topical application thereto, which composition comprises a skin lightening amount of niacinamide or a precursor thereof which is capable of releasing niacinamide of the skin, and a sunburn or santan protective amount of an ultra-violet absorbing sunscreen together with a mutually compatible cosmetically acceptable vehicle.

Niacinamide is the amide of niacin which is also known as nicotinamide or pyridine-3-carboxylic acid.

An example of a niacinamide releasing compound is niacinamide ascorbate.

The amount of niacinamide in the composition either as the niacinamide itself or a precursor thereof which is capable of releasing niacinamide on the skin should be sufficient to lighten the skin when the composition is applied to a human subject. For the skin lightening effect to be apparent, the skin will normally be that of a dark skinned subject, for example of Indian, West Indian or Negroid origin. It may furthermore be necessary for the composition to be applied repeatedly to the same area of skin, for example daily for 2 weeks, before skin lightening becomes evident. Hence the amount of niacinamide or its precursor present in the composition which constitutes a skin lightening amount can vary from subject to subject.

We have found that for general purposes, the amount of niacinamide or its precursor should be from about 0.1% to about 10% by weight of the composition, preferably from about 0.5 to about 5%.

In the following description the term "niacinamide" will include niacinamide itself or a precursor thereof which is capable of releasing niacinamide on the skin unless stated otherwise.

The ultra-violet absorbing sunscreen is preferably an ultra-violet absorber absorbing in the rang of 290–320 nm, which provides burn prevention properties. Preferably, this ultra-violet absorber is urocanic acid and/or a compound of the following formula:

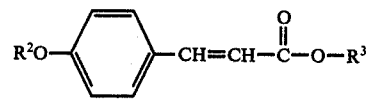

where $R^2$ is alkyl containing from 1 to 4 carbon atoms, preferably $CH_3$, and $R^3$ is alkyl containing from 4 to 10 carbon atoms, preferably $C_6H_{13}$ or an alkoxyalkyl group of the type $—R^4—O—R^5$ wherein $R^4$ is alkylene containing from 1 to 4 carbon atoms and $R^5$ is alkyl containing from 1 to 4 carbon atoms.

To endow the compositions with tanning prevention properties, an ultra-violet absorbing sunscreen having maximum absorption in the tanning ray region of the spectrum, viz. 320-360 nm can be used. Examples of such compounds have the following formula:

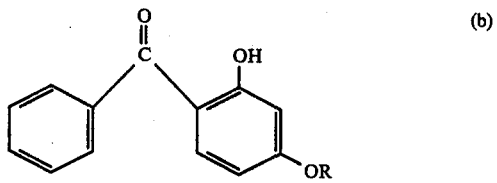

where R is alkyl containing from 4 to 12 carbon atoms, preferably $C_8H_{17}$.

These general classes of ultra-violet absorber will hereinafter be referred to a "uv absorbers (a)" and "(b)" respectively.

Of the foregoing examples, the preferred UV absorbers (a) are selected from urocanic acid, and 2-ethoxyethyl-p-methoxy-cinnamate available for example from Givaudin as GIVTAN F. For compositions having tanning prevention properties, 2-hydroxy-4-octyloxybenzophenone, available for example as CYASORB 531 from the American Cyanamic Company is the preferred uv absorber (b).

Niacinamide can be formulated together with urocanic acid, a uv absorber (a) or a uv absorber (b) or preferably with a mixture comprising at least one uv absorber which absorbs in each part of the spectrum as herein described.

The advantages of using niacinamide in association with a uv absorber in each of the ranges 290–230 nm and 320–360 nm, is that the resultant skin composition not only lightens the skin, but protects it from both tanning and burning rays.

Appropriate amounts of uv absorber (a) are from about 0.1 to about 4% by weight of the composition and of uv absorber (b) about 0.1 to about 4% by weight of the composition, and when urocanic acid is used, it can be from about 0.1 to about 10% by weight of the composition.

The vehicle which forms part of the cosmetic composition is one or more substances which are mutually compatible with the niacinamide and the sunscreen and which are also cosmetically acceptable in that they will not harm the skin. The vehicle can act as a diluent, dispersant or carrier for the other ingredients of the composition, and is therefore intended to ensure that they can be readily applied to and distributed evenly over the skin at an appropriate concentration.

The vehicles that can be used in compositions according to the invention can include water, powder absorbents, binders and carriers, and liquids such as emollients, propellants, solvents, humectants and thickeners. Examples of each of these types of vehicles are as follows:

Powder Absorbents

Magnesium silicate
Lanolin absorption base
Amorphous silica powder

Powder Binders and Carriers

Microcrystalline cellulose
Isostearyl neopentanoate
Polyacrylamide
Lauryl lactate
Precipitated silica
Talc
Chalk

Emollients

Stearyl alcohol
Glyceryl monoricinoleate
Glyceryl monostearate
Sulphated tallow
Propylene glycol
Mink oil
Cetyl alcohol
Stearyl stearate
Isopropyl isostearate
Dimethyl brassylate
Stearic acid
Isobutyl palmitate
Isocetyl stearate
Oleyl alcohol
Isopropyl laurate
Hexyl laurate
Decyl oleate
Di-isopropyl adipate
2-octadodecanol
Iso-cetyl alcohol
Myristyl ethoxymyristate
Cetyl palmitate
Dimethylpolysiloxane
Di-isopropyl adipate
Di-n-butyl sabacate
Di-isopropyl sebacate
Di-2-ethyl hexyl sebacate
2-ethyl hexyl palmitate
Isononyl isononanoate
Isodecyl isononanoate
Isotridecyl isononanoate
2-ethyl hexyl palmitate
2-ethyl hexyl stearate
Di-(2-ethyl hexyl) adipate
Di-(2-ethyl hexyl) succinate
Isopropyl myristate
Isopropyl palmitate
Isopropyl stearate
Butyl stearate
Glyceryl monostearate
Polyethylene glycols
Propylene glycol
Triethylene glycol
Lanolin
Castor oil
Acetylated lanolin alcohols
Acetylated lanolin
Petrolatum
Isopropyl ester of lanolin fatty acids
Mineral oils
Butyl myristate
Isostearic acid
Palmitic acid
Isopropyl linoleate
Cetyl lactate
Lauryl lactate
Myristyl lactate
Quaternised hydroxy alkyl aminogluconate
Decyl oleate
Isodecyl oleate Di-isopropyl adipate
2-ethyl hexyl palmitate
Isostearyl neo pentanoate
Myristyl myristate
Di-isopropyl adipate
Oleyl ethoxy myristate
Diglycol stearate
Ethylene glycol monostearate
Myristyl stearate
Isopropyl lanolate

Propellants

Trichlorofluoro methane
Dichloro difluoro methane
Dichloro tetrafluoro ethane
Monochloro difluoro methane
Trichloro trifluoro ethane
Propane
Butane Isobutane
(used singly or in admixture)

Solvents

Ethyl alcohol
2-ethylhexanol
Ethylene carbonate
Propylene carbonate
Castor oil
Linear ethoxylated polymer of methanol
Ethylene glycol monoethyl ether
Diethylene glycol monobutyl ether
Diethylene glycol monoethyl ether
Propoxylated butanol
Propoxylated oleyl alcohol
Butyl stearate
Butyl myristate

Humectants

Glycerin
Sorbitol
Sodium 2-pyrrolidone-5-carboxylate
Soluble collagen
Dibutyl phthalate
Gelatin
Polyglycerogen
Ethoxylated (10-20 moles) glucose
Propoxylated (10-20 moles) glucose

Thickeners

Gums
Starch
Colloidal silicon dioxide
Sodium polyacrylate
Tetra alkyl and/or trialkyl aryl ammonium smectites
Chemically modified magnesium aluminum silicate
Organically modified montmorillonite clay
Hydrated aluminium silicate
Fumed silica
Carboxy vinyl polymer
Sodium carboxymethyl cellulose
Hydroxyethyl stearate amide
Ethylene glycol monostearate The quantity of vehicle employed can constitute the balance of the composition, or a smaller proportion than the balance, provided that the vehicle is capable of performing, if necessary in admixture with other vehicles, its function as herein defined. One of the embodiments of the invention provides for a vehicle containing from about 1 to about 50 percent by weight of an emollient; and from about 10 to about 70 percent by weight of water.

Compositions according to the invention can be prepared for topical application to the skin in the form of conventional product types such as creams, lotions, ointments and aerosol products.

The invention is further illustrated by reference to the following example of a cosmetic cream.

|  | % by weight |
|---|---|
| Stearic acid | 15.0 |
| Cetyl alcohol | 0.5 |
| CYASORB UV 531 | 0.4 |
| GIVTAN F | 1.0 |
| Glycerol | 1.0 |
| Niacinamide | 3.0 |
| Isopropyl myristate | 4.0 |
| Glyceryl monostearate | 1.0 |
| Caustic Potash (17.8%) | 2.8 |
| Formalin | 0.05 |

-continued

|  | % by weight |
|---|---|
| Perfume | 0.2 |
| Distilled water | to 100 |

The skin lightening effect of compositions according to the invention has been demonstrated in clinical testing in human subjects against a placebo without any actives. The skin lightening effect is gradual and reversible — the colour of the skin returning to normal a few weeks after discontinuing use of this cream. The composition based on the invention provides a safe and gradual means of obtaining a fairer complexion.

What is claimed is:

1. A cosmetic composition for application to the skin, comprising:
    (a) from about 0.5 percent to about 5 percent by weight of niacinamide, or a precursor thereof;
    (b) from about 0.1 to about 10 percent by weight of an ultraviolet absorbing sunscreen; and
    (c) a cosmetically acceptable vehicle.
2. The cosmetic composition according to claim 1, wherein the precursor is niacinamide ascorbate.
3. The cosmetic composition according to claim 1, wherein the sunburn or suntan protective amount is from about 0.1 to about 4% by weight of the composition.
4. The cosmetic composition according to claim 1, wherein the sunscreen is a compound absorbing within the ultraviolet range between 290 and 320 nm.
5. The cosmetic composition according to claim 4, wherein the sunscreen is selected from urocanic acid, 2-ethoxyethyl-p-methoxycinnamate and mixtures thereof.
6. The cosmetic composition according to claim 1, wherein the sunscreen is a compound absorbing within the ultra-violet range between 320 and 360 nm.
7. The cosmetic composition according to claim 6, wherein the sunscreen is 2-hydroxy-4-octyloxybenzophenone.
8. The cosmetic composition according to claim 1, comprising
    (i) from about 0.5 to about 5% by weight of niacinamide;
    (ii) from about 0.1 to about 4% by weight of 2-ethoxyethyl-p-methoxycinnamate; and
    (iii) from about 0.1 to about 4% by weight of 2-hydroxy-4-octyloxybenzophenone;
    (iv) as a vehicle, from about 1 to about 50% by weight of an emollient; and
    (v) from about 10 to about 70% by weight of water.
9. A method of lightening the skin which comprises applying to the skin a composition containing
    (a) a skin lightening amount of niacinamide, or a precursor thereof which is capable of releasing on the skin a corresponding amount of niacinamide, and
    (b) a cosmetically acceptable vehicle.
10. A method of lightening the skin which comprises applying to the skin a composition containing
    (a) from about 0.1 percent to from about 10 percent of niacinamide, or a precursor thereof, and
    (b) a cosmetically acceptable vehicle.
11. A method according to claim 10, wherein said composition additionally contains a sunburn or suntan protective amount of an ultraviolet absorbing sunscreen.

12. A method according to claim 11, wherein said sunburn or suntan protective amount is from about 0.1 percent to from about 10 percent by weight of said composition.

13. A method according to claim 12, wherein said sunscreen is a compound absorbing within the ultraviolet range between 290 and 320 nm.

14. A method according to claim 13 wherein said sunscreen is a compound selected from the group consisting of urocanic acid, 2-ethoxyethyl-p-methoxycinnamate, and mixtures thereof.

15. A method according to claim 12, wherein said sunscreen is a compound absorbing within the ultraviolet range between 320 and 360 nm.

16. A method according to claim 15, wherein said sunscreen is 2-hydroxy-4-octyloxy-benzophenone.

17. A method according to claim 10, wherein said precursor is niacinamide ascorbate.

18. A method according to claim 10, wherein said composition contains
(a) from about 0.5 percent to about 5 percent by weight of niacinamide;
(b) from about 0.1 percent to about 4 percent by weight of 2-ethoxyethyl-p-methoxycinnamate; and
(c) from 0.1 percent to from about 4 percent by weight of 2-hydroxy-4-octyloxybenzophenone; and wherein said vehicle contains
(d) from about 1 to about 50 percent by weight of an emollient; and
(e) from about 10 percent to about 70 percent by weight of water.

* * * * *